(12) United States Patent
Frone et al.

(10) Patent No.: US 11,721,433 B2
(45) Date of Patent: Aug. 8, 2023

(54) SYSTEM AND METHOD FOR CONDITION BASED MONITORING AND MAINTENANCE OF AN AUTOMATION TRACK

(71) Applicant: Siemens Healthcare Diagnostics Inc., Tarrytown, NY (US)

(72) Inventors: Shannon Frone, Long Valley, NJ (US); Baris Yagci, Montclair, NJ (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 1239 days.

(21) Appl. No.: 16/319,301

(22) PCT Filed: Jul. 19, 2017

(86) PCT No.: PCT/US2017/042941
§ 371 (c)(1),
(2) Date: Jan. 18, 2019

(87) PCT Pub. No.: WO2018/017770
PCT Pub. Date: Jan. 25, 2018

(65) Prior Publication Data
US 2019/0237190 A1    Aug. 1, 2019

Related U.S. Application Data

(60) Provisional application No. 62/365,310, filed on Jul. 21, 2016.

(51) Int. Cl.
*G16H 40/40*   (2018.01)
*G01N 35/04*   (2006.01)
(Continued)

(52) U.S. Cl.
CPC ....... *G16H 40/40* (2018.01); *G01N 35/00623* (2013.01); *G01N 35/00871* (2013.01);
(Continued)

(58) Field of Classification Search
CPC ........ G16H 40/40; G16H 40/00; G16H 10/40; G16H 10/00; G01N 35/00623;
(Continued)

(56) References Cited

U.S. PATENT DOCUMENTS 5,502,613 A * 3/1996 Saitoh ................... B60L 13/04
                                                                 104/284
5,862,028 A * 1/1999 Kalsi ..................... H02H 7/001
                                                                  361/19
(Continued)

FOREIGN PATENT DOCUMENTS

CN    101910842 A     12/2010
CN    101997386 A     3/2011
(Continued)

OTHER PUBLICATIONS

PCT International Search Report and Written Opinion dated Sep. 29, 2017 (10 Pages).
(Continued)

*Primary Examiner* — Mohamed Charioui

(57) ABSTRACT

Systems and methods for use in an in vitro diagnostics setting incorporating existing or additional sensors in an automation system to assess the health and maintenance status of the automation system are disclosed. Such systems include any of a variety of sensors, such as Hall Effect sensors, temperature probes/thermocouples, ohm meters, volt meters, etc., which are in communication with a local or preferably remote monitoring station that can alert a user or maintenance personnel of needed service.

20 Claims, 14 Drawing Sheets

(51) Int. Cl.
*G16H 10/40* (2018.01)
*G01N 35/00* (2006.01)

(52) U.S. Cl.
CPC .............. *G01N 35/04* (2013.01); *G16H 10/40* (2018.01); *G01N 2035/009* (2013.01); *G01N 2035/00643* (2013.01); *G01N 2035/00881* (2013.01); *G01N 2035/0467* (2013.01); *G01N 2035/0477* (2013.01)

(58) Field of Classification Search
CPC ....... G01N 35/00594; G01N 35/00584; G01N 35/00; G01N 35/00871; G01N 35/04; G01N 2035/00643; G01N 2035/00881; G01N 2035/009; G01N 2035/0467; G01N 2035/0477; G01N 2035/0474; G01N 35/02
See application file for complete search history.

(56) References Cited

U.S. PATENT DOCUMENTS

| | | | |
|---|---|---|---|
| 6,191,507 | B1 | 2/2001 | Peltier et al. |
| 9,346,371 | B2 | 5/2016 | King et al. |
| 2003/0157721 | A1 | 8/2003 | Turner et al. |
| 2008/0148990 | A1 | 6/2008 | Wamble et al. |
| 2010/0236445 | A1* | 9/2010 | King ................ B60L 13/10 104/130.03 |
| 2012/0143029 | A1 | 6/2012 | Silverstein et al. |
| 2013/0078624 | A1 | 3/2013 | Holmes et al. |
| 2014/0065017 | A1 | 3/2014 | Herz et al. |
| 2014/0184223 | A1 | 7/2014 | Otvos et al. |
| 2015/0008768 | A1 | 1/2015 | Achterberg et al. |
| 2015/0243539 | A1 | 8/2015 | Hosek |
| 2015/0273691 | A1* | 10/2015 | Pollack ............... B25J 11/0085 901/41 |
| 2016/0077120 | A1 | 3/2016 | Riether |
| 2016/0180686 | A1 | 6/2016 | Penning et al. |

FOREIGN PATENT DOCUMENTS

| | | |
|---|---|---|
| CN | 102238892 A | 11/2011 |
| CN | 102273062 A | 12/2011 |
| CN | 102358206 A | 2/2012 |
| CN | 102387973 A | 3/2012 |
| CN | 102541024 A | 7/2012 |
| CN | 102556115 A | 7/2012 |
| CN | 102665535 A | 9/2012 |
| CN | 103217656 A | 7/2013 |
| CN | 103635798 A | 3/2014 |
| CN | 103946364 A | 7/2014 |
| CN | 105547782 A | 5/2016 |
| DE | 102012025326 A1 | 6/2014 |
| JP | H0636926 A | 2/1994 |
| JP | H06119573 A | 4/1994 |
| JP | 2001-337725 A | 12/2001 |
| JP | 2008 070329 A | 3/2008 |
| JP | 2008070329 A * | 3/2008 |
| JP | 2009-227415 A | 10/2009 |
| JP | 2009246162 A | 10/2009 |
| JP | 2013-104795 A | 5/2013 |
| JP | 2013-257157 A | 12/2013 |
| JP | 2014-513311 A | 5/2014 |
| JP | 2015-510590 A | 4/2015 |
| WO | 9627544 A1 | 9/1996 |
| WO | 2013151920 A1 | 10/2013 |
| WO | 2016/041933 A1 | 3/2016 |

OTHER PUBLICATIONS

Wu Wenqi, "New Technologies Abroad in Railway Signals", China Railway Publishing House, pp. 86-88, Aug. 31, 2000. (See p. 13 of the English translation of the corresponding Chinese office action). English translation of Chinese Office Action of corresponding Chinese patent Application No. 201780045070.0 17 Pages.
Weirong He: "Application of Online Contactless Monitoring in Metro Electrical Equipment"; Urban Mass Transit, Issue 6, Maintenance Support Centre; Shangai; China; Jun. 6, 2012.
Extended EP Search Report dated Aug. 8, 2019 of corresponding European Application No. 17831836.6, 4 Pages.

* cited by examiner

SYSTEM AND METHOD FOR CONDITION BASED MONITORING AND MAINTENANCE OF AN AUTOMATION TRACK

CROSS-REFERENCE TO RELATED APPLICATIONS

This application claims the benefit of U.S. Provisional Application Ser. No. 62/365,310 filed Jul. 21, 2016, which is incorporated herein by reference in its entirety.

TECHNOLOGY FIELD

The present disclosure relates in general to systems and methods used to monitor and maintain an automation system particularly for use in a laboratory environment, and more particularly, to automation systems for assisting in the transport and interaction with patient samples and/or reagents for in vitro diagnostics in a clinical analyzer.

BACKGROUND

In vitro diagnostics (IVD) allow labs to assist in the diagnosis of disease based on assays performed on patient fluid samples. IVD includes various types of analytical tests and assays related to patient diagnosis and therapy that can be performed by analysis of a liquid sample taken from a patient's bodily fluids, or abscesses. These assays are typically conducted with automated clinical chemistry analyzers (analyzers) onto which fluid containers, such as tubes or vials, containing patient samples have been loaded. The analyzer extracts a liquid sample from sample vessels and combines the sample with various reagents in special reaction cuvettes or tubes (referred to, generally, as reaction vessels). In some conventional systems, a modular approach is used for analyzers. A lab automation system can shuttle samples between one sample processing module (module) and another module. Modules may include one or more stations, including sample handling stations and testing stations (e.g., a unit that can specialize in certain types of assays or can otherwise provide testing services to the larger analyzer, which may include immunoassay (IA) and clinical chemistry (CC) stations.

An automation system for use with analyzers in an IVD environment moves tubes containing sample specimens between different stations within an analyzer or between analyzers. One method of transporting sample and reagent tubes is on a carrier, or vessel mover (VM), moved about via a magnetic track system. Such a system involves permanent magnets as well as complex electromagnets, which operate to facilitate movement of the vehicle mover about the track, as desired.

As such, the condition of the automation system and/or its component parts, such as the track, the electronics, etc., are vital to the operation of not only the automation system, but the overall IVD system.

Thus, there is a need to monitor and maintain the automation system and its components.

SUMMARY

Some embodiments provide an automation system for use in an in vitro diagnostics setting comprising an automation track.

A maintenance monitoring system for an IVD system employs a variety of sensors. The maintenance monitoring system includes a monitoring station comprising a process controller (PC) capable of receiving, displaying, and storing data from the variety of sensors.

In some embodiments, the data displayed is any one of motor status, coil board temperature, and deflected magnetic field strength. In some embodiments, the system is adapted for monitoring two or more IVD systems. In some embodiments, the monitoring station is remote from the IVD system.

Some embodiments provide a system comprising two or more independent IVD systems, each having an automation system employing one or more sensors, one or more controller modules, and one or more node controllers; and a monitoring station PC adapted and configured for receiving, storing, and displaying data from the one or more sensors, one or more controller modules, and one or more node controllers of each IVD system. In some embodiments, each of the two or more independent IVD systems is located separately from the others and the monitoring station PC.

Some embodiments provide a method for monitoring the health of a vessel mover system in an IVD system comprising collecting data from one or more sensors in the vessel mover system, receiving data via a monitoring station PC capable of receiving, displaying, and storing data from the one or more sensors, comparing the collected data to known evaluation standards, and sending an audible or visual alert, as appropriate, based on the comparison.

In some embodiments, a maintenance monitoring system for an in-vitro diagnostics (IVD) system includes an automation system that provides a track along which a plurality of carriers traverse, each carrier having one or more magnets in a base of each carrier, and a plurality of coil boards mounted to the track, each board having one or more magnetic coils arranged along the longitudinal direction of the track and configured to selectively engage the one or more magnets in the base of each carrier, and at least one sensor. The system includes at least one controller coupled to each of the plurality of coil boards, the controller configured to selectively activate the magnetic coils of each coil board and to collect sensor data from each sensor of each coil board, and at least one processor configured to store the sensor data in memory, analyze the sensor data to identify any coil boards that are performing outside normal parameters from the sensor data, and alert an operator automatically if any such identified coil boards.

In some embodiments, a maintenance monitoring system for an in-vitro diagnostics (IVD) system, provides an automation system having a track along which a plurality of carriers traverse, each carrier having one or more magnets in a base of each carrier, and a plurality of coil boards mounted to the track, each board comprising a plurality of magnetic coils configured to selectively engage the one or more magnets in the base of each carrier, and at least one sensor. Additionally, a plurality of controllers, each coupled to a subset of the plurality of coil boards, are configured to control the magnetic coils of each coil board in the subset and to collect sensor data from each sensor of each coil board and to transmit the sensor data. A central processor configured to receive, store, and analyze the sensor data to identify any coil boards that are performing outside normal parameters from the sensor data, while a user interface configured to alert an operator automatically if any coil boards have been identified. A central processor can be a processor that provides centralized analysis or storage of data relative to the automation system, where coil boards are physically spread throughout the automation system. By providing a centralized processor, aggregated data about multiple coil boards, such as all coil boards in a given automation system or from multiple automation systems within an organization, can be provided. The central processor can be separated from the coil boards or master boards having the controllers for the coil boards via an IP network, Ethernet network, or the Internet.

In some embodiments, the processor alerts the operator by displaying data comprising is any of motor status, coil board temperature, and magnetic field strength. In some embodiments, the sensor is a Hall Effect sensor.

In some embodiments, the processor is adapted for monitoring two or more IVD systems. In some embodiments, the processor is separated from the controller and coil boards by the Internet. In some embodiments, the processor is further configured to request maintenance across a network if any coil boards are determined to be performing outside normal parameters. Exemplary parameters include expected magnetic field strength, temperature range, current, or voltage, which would be expected for a coil board operating in a nominal range.

In some embodiments, the processor is part of a console with a user interface used by an operator of the IVD system. Such a console can include a computer interface (e.g., screen with GUI and input devices such as touch screen, buttons, keyboard, mouse or the like). In some embodiments, the system further includes a second independent automation system comprising a second track and a second plurality of coil boards that transmit sensor data to the at least one processor over a network.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

An automation system for use with analyzers in an IVD environment moves tubes containing sample specimens between different stations within an analyzer or between analyzers. One method of transporting sample and reagent tubes is on a carrier, or vessel mover (VM), moved about via a magnetic track system. Such a system involves permanent magnets as well as complex electromagnets, which operate to facilitate movement of the vehicle mover about the track, as desired.

Figure 1:
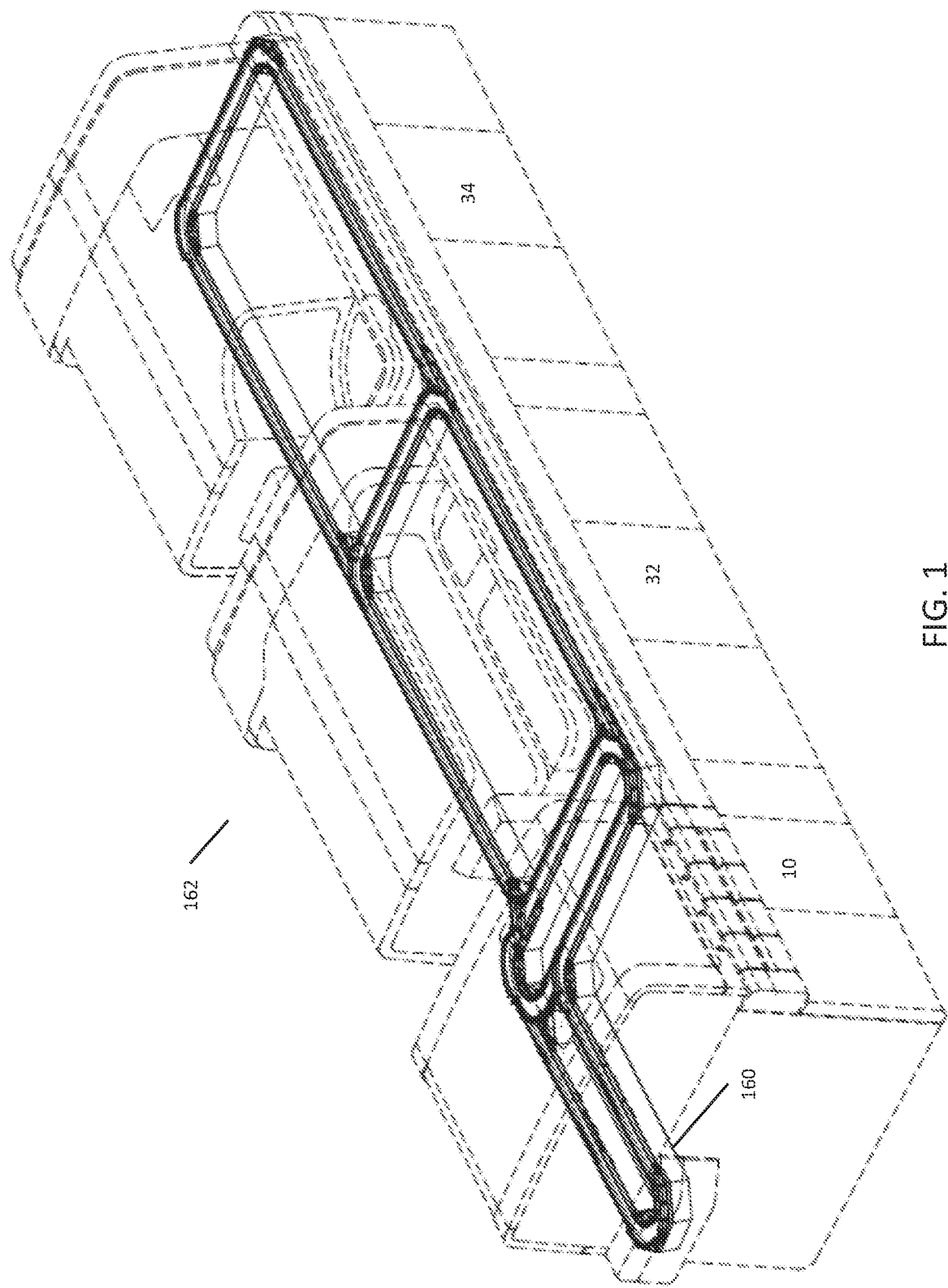
FIG. 1 is a perspective view of an exemplary automation track system for use with some embodiments.

FIG. 1 depicts an exemplary IVD system employing a magnetic vessel moving (VM) system. This particular arrangement shows an analyzer system 162 having three instrument modules, a sample handler 10, a clinical chemistry module 32, and immunoassay module 34, each having a cover, shown in dashed lines. The track of the magnetic vessel moving system 160 is shown as making several loops, which essentially surround the working parts of the instruments. The track defines multiple pathways defined by portions of track, track switching mechanisms, and other parts of the automation system.

As stated in the description of the VM system, below, a number of sensors are employed for the regular operation and error handling; additional sensors may be added, as desired. Sensors useful for the monitoring of the automation system health may include voltage meters, ohm meters, thermometers or thermocouples, switches, gauges, humidity sensors, Hall Effect sensors (HES), etc.

The automation system is the backbone of an IVD platform; it is important that the VM is operational whenever the instrument is in use. To extend the uptime and avoid unscheduled service visits, certain aspects of the track health are monitored periodically. The deviation in the monitored parameters indicates a possible problem in certain components of the track, and triggers a scheduled service visit. The methods and system disclosed herein are designed to monitor these parameters and send results and/or alarms to a central location where it can be determined whether a service visit is recommended. Such a visit keeps the customers satisfied and the service costs down.

Some parameters that may be monitored include, but are not limited to, motor status, impedance, coil coupling, temperature, coil board temperature, I/O status, etc.

Under current industry practice, customers call service after the occurrence of a failure. In other cases, a customer service technician realizes a budding problem while fixing other problems. With the proactive monitoring methods and systems disclosed herein, data-based and predictable system maintenance can be arranged, without relying on the serendipitous presence of a service technician.

In some embodiments, existing automation systems employ measurement circuitry to check the health of the coils that make up the electromagnets in the track, use Hall Effect sensors (HES) to monitor magnetic field deflection created by activated coils, and/or a thermometer/thermocouple to monitor the temperature of the coil boards to check if the operating temperatures are as expected. Existing sensors provide important information such as current measurement, deflected magnetic field, temperature, etc. Some methods and systems disclosed herein take advantage of these existing sensors, and may employ additional sensors, as needed, for the purpose of diagnosing problems and maintaining the health of the VM system.

By using sensors needed for normal operation, and already present in the automation system, there is little, if any, increase in the total cost of the overall device, and no increase in the number of parts. Therefore, there is no negative impact on reliability.

In some embodiments, the VM track uses data collected from these sensors that can be communicated locally or remotely to a central operations monitoring or maintenance monitoring center. The data can be reviewed for immediate action and/or compiled for statistical and/or trend analysis.

Embodiments can utilize distributed power sources. Each track section is associated with an analyzer module or a sample handler module. Standalone track sections placed between these modules can be associated with either type of module. Each track section is powered by the module to which it is physically resident, as well as one adjacent module. In some embodiments, determining which adjacent module to draw redundant power from utilizes the following convention. Looking at the boundary between analyzer modules and sample handler modules (e.g., track section 36), the adjacent module that provides redundant power will always be the module nearest that boundary. Each track section is powered by the current module and the module prior. Here "prior" is described as the module closer to the sample handler (SH)/analyzer module boundary. The U-shaped track around an analytical module is powered through the power source of that analyzer. As a backup, the U-shape is connected to the previous analyzer power source. The controller module at each power source can identify a local power failure and automatically switch over to the adjacent redundant power source. For example, if the current analytical module needs to be taken offline for service, or is down due to an internal failure, then the power controller for each track section will switch the power source for the track to the power source provided by the previous/adjacent instrument. This way, the track operations can continue even if one of the power sources is down. In some embodiments, the power system module for each U-shaped track is located proximate to the straight track section at the back of the instrument. The power is distributed to the linear motor in the front of the analyzer from the power controller. A power cable can be routed through the analytical module itself to that front track section. In some embodiments, each track section works with 24 VDC, which provides sufficient power to each carrier to allow it to reach a maximum speed on straight track sections of 6 m/s.

In some embodiments, track sections are divided up into a number of coil boards. A coil board includes a linear array of coils that can be mounted underneath the metallic (non-ferromagnetic) surface of the track. For straight sections of track, each coil board is straight, while in corners or curves, coil boards include appropriately laid out coils to match the curve. All coil boards are controlled by master boards and node controllers. In some embodiments, each master board can control up to eight different coil boards. Meanwhile, a node controller is centralized. A single node controller can control the entire vessel mover track. In some embodiments, multiple distributed node controllers can be used for expandability. For example, in larger systems, where the track extends for several meters, multiple node controllers may be used and control of carriers can be handed off as they traverse different regions of the track network.

Vessel mover manager software can reside on the host PC that communicates with the node controller for the physical track through a network switch. In some embodiments, multiple node controllers can be used for redundant failover, with a single node controller handling normal duty, while a second alternate node controller is prepared to take over should the primary node controller fail. In some embodiments, the primary and secondary node controllers can have the exact same software operation and design, but different IP addresses, allowing seamless failover. Each node controller is connected to the master boards through network switches within the analyzer system. In some embodiments, there are two layers of network switches. A top level Ethernet switch is part of the central utility center for the process control manager (PCM) system. This can be connected to a series of gigabit Ethernet switches in daisy chained fashion. Each of these switches can serve double duty as the power controller for each module, providing both network switching and failover power control. In this arrangement, each gigabit switch is connected to each switch in the adjacent modules. While this daisy-chained arrangement may result in broken communications should a network switch fail, these switches can be designed to be hot-swappable for easy resolution. Moreover, the expected failure rate of these network switches is much lower than the power systems of each module. The linear motors that make up the track can communicate with each local master board via these gigabit switches.

Figure 2:
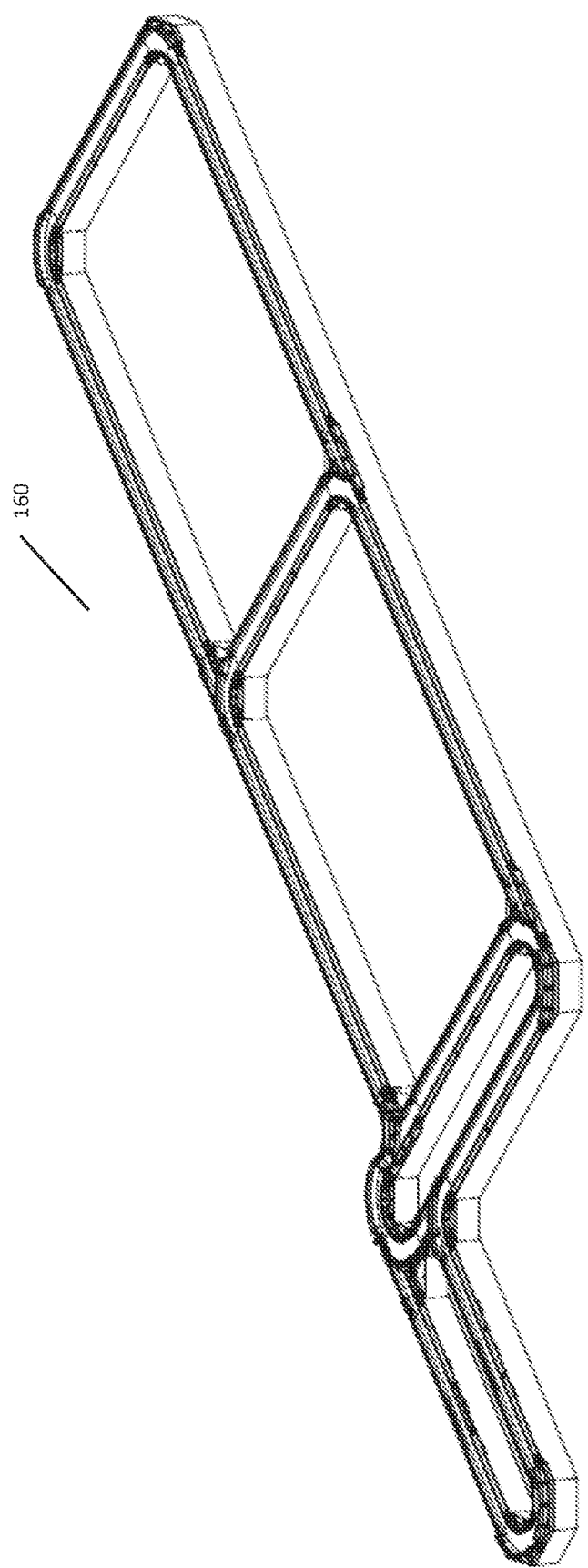
FIG. 2 is a perspective view of an exemplary automation track system for use with some embodiments.

FIG. 2 shows a perspective view of track system 160. Track system 160 is configured to have a single sample handler unit and two analyzer modules. FIG. 1 shows track system 160 situated in a fully operational analyzer system 162 that includes a sample handler module 10 and two analyzer modules of 32 and 34. As can be seen, track system 160 is housed within the modules themselves such that the track is not easily accessible to an operator. However, track 160 and analyzer system 162 utilize a modular design, whereby track components reside within each module and each module can easily be linked together to join the track segments by placing adjacent modules proximally and linking them. Lids above track 160 can be removed during installation or service to facilitate linking of tracks. In some embodiments, track sections are expanded by placing modules adjacent to one another and bolting the track sections of each module together, forming a single multi-branching track system, such as track 160. Signaling cables can be daisy-chained together for ease of expanding control.

Figure 3:
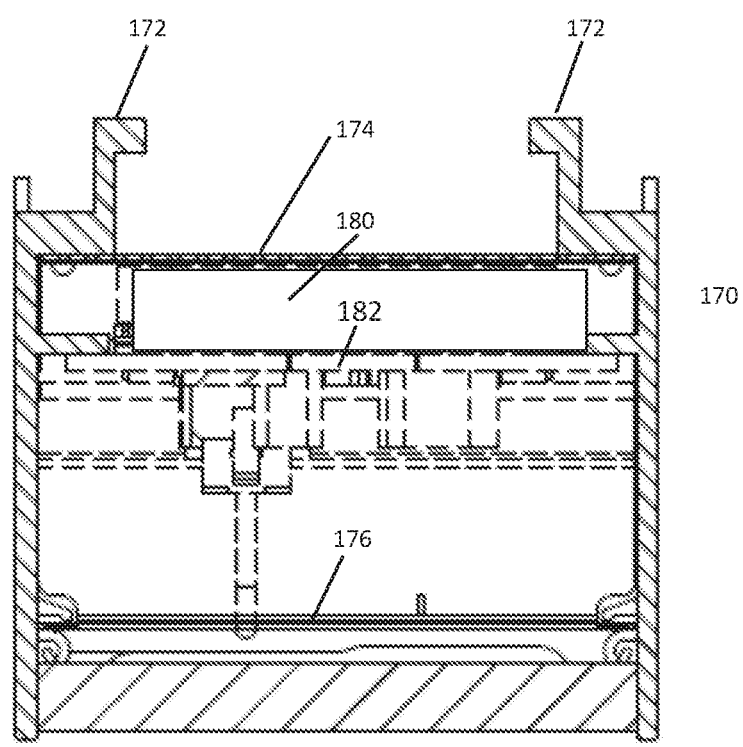
FIG. 3 is a cross sectional view of an exemplary automation track system for use with some embodiments.

FIG. 3 shows a cross-sectional view of the track section 170. Track section 170 may be a track section used in track 160. In this embodiment, carriers ride between rails 172 on a track surface 174. In some embodiments, rails 172 are aluminum extrusions that also include vertical sides on the exterior of the track components underneath track surface 174. These aluminum extrusions can include brackets to easily bolt internal components to these side pieces to form a track unit. Track surface 174 is preferably a stainless steel (non-ferromagnetic) surface, making it durable and easy to clean. It should be appreciated that other materials can be used for rails 172 and track surface 174, such as aluminum, stainless steel, composite materials, etc. At the bottom of the side components of rails 172 resides a baseplate 176. Baseplate 176 can be mounted to the modules containing track section 170, and provides support for the track system.

Beneath track surface 174 resides a series of coils 180. The longitudinal direction of track section 170 is into the page; as you travel along the track section 170, you encounter additional coils 180. Coils 180 are preferably mounted to coil boards 182 and are preferably laterally oblong, allowing more coils to be placed longitudinally along the track. In some embodiments, coil boards 182 are printed circuit boards (PCBs) that include several coils 180 in the longitudinal direction. An exemplary coil board is 250 mm in length, accommodating all of the coils 180 needed for 250 mm of track. Thus, a typical track section will have several coil boards 182, to make up an entire track system. In some embodiments, coil boards 182 receive a control signal to indicate the trajectory to apply to a carrier traveling along that coil board and a power source of 24 VDC. Coil boards 182 include coils 180, motor drivers to drive those coils, and one or more sensors to detect the presence of carriers traversing the track surface above the coil board. These sensors can include Hall Effect sensors (HES) to detect the presence and location of the carrier traveling along the coil board via the magnets in the carrier. Accordingly, there may be more sensors than coils, allowing fine resolution of the position of a carrier traversing track surface 174. Furthermore, an RFID receiver may be utilized to receive an RFID signal that identifies the carrier traveling along the track surface. In some embodiments, magnetic signatures unique to each carrier can be detected by the Hall Effect sensors to determine the identity of the carrier magnetically. For example, a carrier traversing an array of Hall Effect sensors can be characterized at manufacturing to identify a unique signature of that carrier, based on rise times and signal artifacts that are detected by the Hall Effect or sensor array as magnets in the carrier travel over that array. In some embodiments, smaller magnets than the main drive magnets may be placed in the bottom portion of a carrier to intentionally create a unique signature for each carrier at manufacturing. This magnetic signature can be correlated to an identity of each carrier in software for the vessel mover system. An exemplary linear synchronous motor drive system is described in U.S. Pat. No. 9,346,371.

Figure 4:
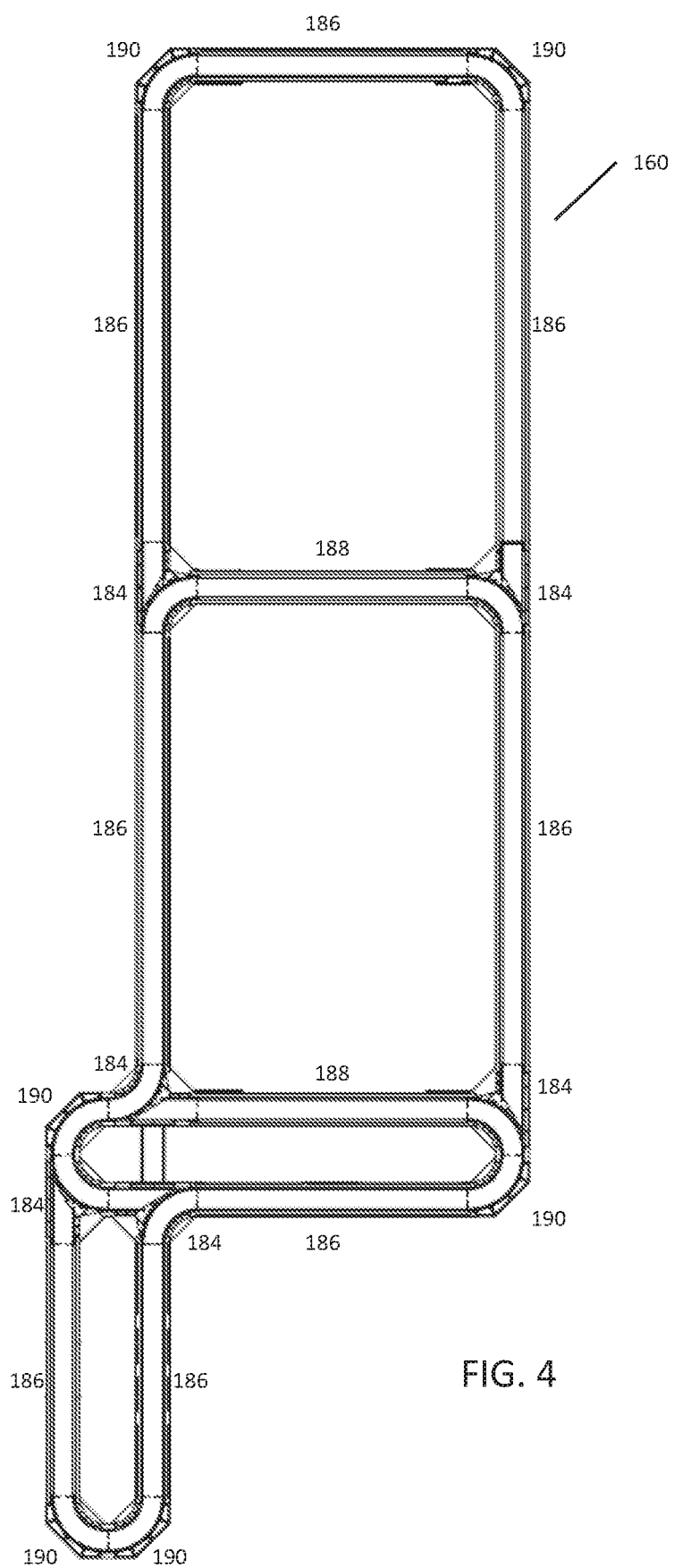
FIG. 4 is a top down view of an exemplary automation track system for use with some embodiments.

FIG. 4 shows a top view of an exemplary track system 160 with the individual track sections identified. There are, generally, four types of track sections that make up the modular design of track system 160. Switching segments 184 are branches in the track. The track surface for switching segments 184 is generally T-shaped, with rounded inside edges. Meanwhile, the rails of switching segments 184 include one straight rail (top of the T), one radiused rail (one inside corner of the T), and one radiused rail that includes a switching mechanism (other inside corner of the T). This switching mechanism is a movable rail component that can be turned a predetermined number of degrees to act as a switch (e.g., 20-30 degrees, depending on geometry). On one side of the rail component, it acts as a straight rail. On the other side of the rail component, the rail presents itself as a radiused rail forming an outside corner of a turn. By switching this movable rail component, that movable rail component can either provide the outside of a turn, or a simple straight-away rail. Thus, the mobile component provides a binary switch whereby switching segment 184 presents itself as a turn or as a straightaway, depending on the control signal. This can be used to divert individual carriers based on the state of the switching segment. It should be noted that, while the track may be bidirectional, only one end of the T can be connected to the center portion of the T to form a turn. Thus, while switching segments 184 may have three ports, essentially, one port may be switched to either of the other two ports, but those two ports cannot be joined together.

A simpler type of track section is a straightaway, such as outside straightaway 186 or inside straightaway 188. The basic components of straightaways 188 and 186 are, effectively, a series of coil boards providing linear motive forces along the direction of that straightaway. However, straightaways 186 and 188 are identified separately in FIG. 4 because inside straightaways 188 can be operated under the control of the local module, rather than a vessel mover controller that controls the entire track 160, in some embodiments. This allows each local module to independently operate track sections 188 to act as a local random-access queue. The vessel mover controller can hand off control to the local module after moving a carrier from a switching segment 184 to the local inside straightaway 188. Similarly, when a local module has completed aspirations on a sample residing on inside straightaway 188, that module may move the sample carrier into a switching segment 184 and hand off control to the vessel mover controller. In some embodiments, inside track sections 188 still operate under the control of the vessel mover controller that controls the entire track system 160. To control a local queue on inside straightaway 188, the local module can communicate directly with the vessel mover controller to request movement of carriers within track section 188. This allows the local module to manifest control over carriers in its queue by using a request to acknowledge communication system, allowing the vessel mover controller to have expertise in moving individual carriers and operating track system 160.

A fourth type of track segment is a curved track segment 190. Curved track segment 190 provides a 90° bend with a predetermined radius (or other angular bends in some embodiments). This radius is preferably the same as the radius used in turns when switching track segments 184 are switched into a curve. The radius is chosen to minimize the space impact of curves while, at the same time, allowing carriers to move quickly around curves without encountering drastic lateral forces. Thus, the space requirements and speed requirements of automation track 160 can determine the radius of curved segments 190.

Electrically, curved segments 190 are substantially the same as straightaways 186 and 188. Each of these segments includes a plurality of coils that are activated in sequence to provide a linear motor in conjunction with magnets in the bottoms of carriers as each coil is activated to provide a push or pull force on drive magnets placed in the bottom of each carrier. The speed at which coils are activated in sequence determines the speed of the carrier on that section of track. Furthermore, carriers may be moved into a position and stopped at a predetermined location with high resolution by activating coils at that location.

Figure 5:
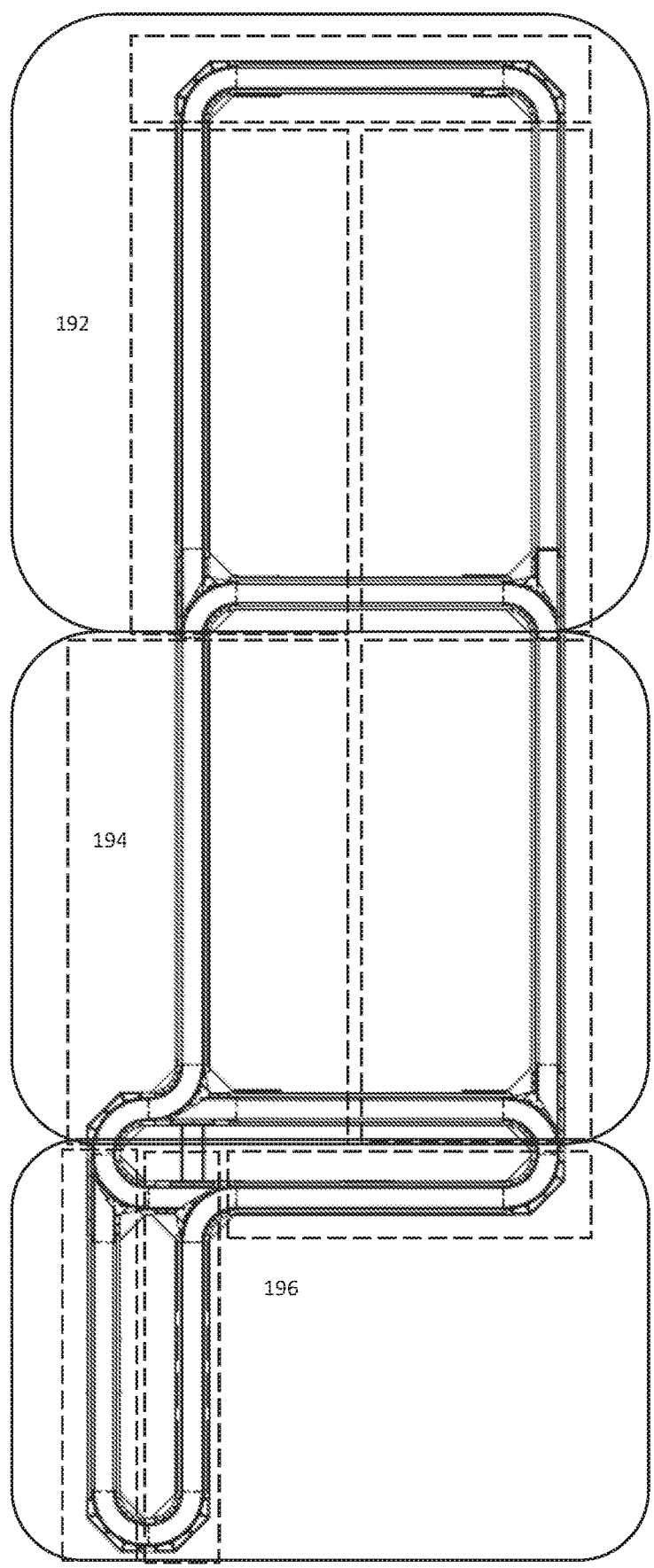
FIG. 5 is a top down view of an exemplary automation track system and some logical parts for use with some embodiments.

FIG. 5 shows the various control zones for a vessel mover controller controlling track 160. Each dashed box represents a different control zone that is controlled by a separate master board. Coil boards within those track segments, or portions of track segments, are operated under the control of a different master board for each control zone. This assists the scalability of track management. A node controller can control several master boards, communicating with them via a network. Meanwhile each master board can control individual coil boards for the region of the track that each master board controls. Each master board can communicate with the coil boards to receive sensor information identifying the position and location of carriers, and manage the trajectory of that carrier via control signals sent to each coil board. Each master board receives trajectory information for local carriers from a node controller. This allows each master board to govern a small section of track, carrying out the real-time control of that section of track, based on the information received from the controller, to handle overall management tasks of the entire track system. In the exemplary embodiment shown in FIG. 5, there are eight master board control zones. Each master board is also responsible for managing any switching track segments 184 within its control zone to direct a carrier to the appropriate point of exchange with the next control zone.

To further divide management of the track system and to provide power failover redundancy, the track system can be divided into different regions, roughly corresponding to each module within the system. Region 192 corresponds to analyzer module 34, while region 194 corresponds to analyzer 32, and region 196 corresponds to sample handler 10. It should be noted that multiple master boards are encompassed within each of these regions. Redundancy can be accomplished by assigning a power failover gigabit Ethernet (PFGE) switch to be in charge of providing network and power to each of these regions. Each PFGE switch provides local networking between each master board and the node controller. Each PFGE switch also provides power to the local region of track. By utilizing a switch to provide power, power redundancy can be achieved. In this example, the PFGE switch for region 196 accesses a local power source to provide power to each master board in this region. That PFGE switch also provides a power channel that may be accessed in the adjacent PFGE switch for region 194. The PFGE switch for region 194 has normal access to a local power source provided by the local analyzer module. Should that local analyzer module fail, be turned off, or need servicing, that power supply can be interrupted. However, it is desirable to still allow analyzer module 34 to operate while analyzer module 32 is being serviced. To accomplish this, the track sections in region 194 and 192 need to continue to operate. To accomplish this, the PFGE switch for region 194 detects the loss of power from the local module, and accesses the power feed supplied by the adjacent PFGE switch from region 196. The PFGE switch for region 194, in turn, provides a power feed to the PFGE switch for region 192, should that section need power when local module power fails. Should module 34 lose power, such that the PFGE switch for region 192 cannot access the local power feed, that PFGE switch can detect the loss of local power and access the power feed supplied by the PFGE switch for adjacent region 194. In this manner, should analyzer module 32 or 34 fail, local track sections continue to get power supplied by the power source for the module in the adjacent region.

Figure 6:
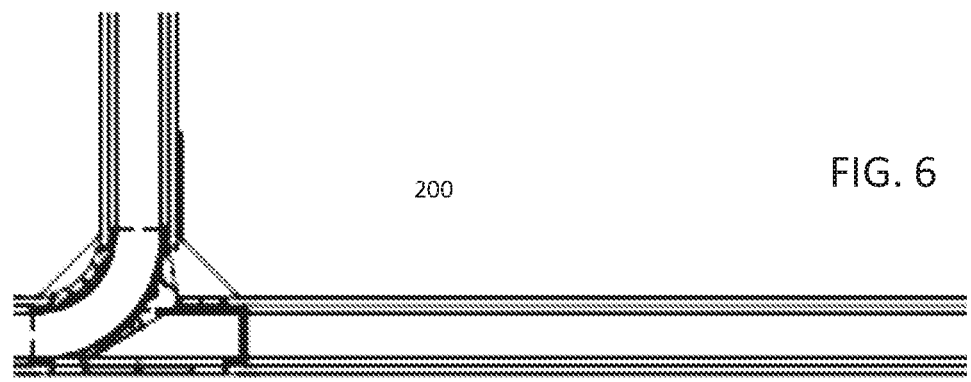
FIG. 6 is a top down view of an exemplary automation track section for use with some embodiments.
Figure 7:
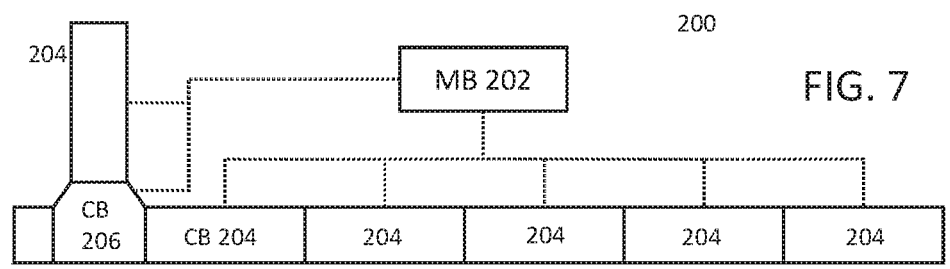
FIG. 7 is an electrical system diagram of an exemplary automation track section for use with some embodiments.

FIG. 6 is a top view of an exemplary portion 200 of track 160. Exemplary track portion 200 includes a plurality of coil boards that are controlled by a single master board. FIG. 7 shows the same exemplary track portion 200 with the coil boards and master board that controls them, with the physical track stripped away. Master board 202 receives control instructions from the vessel mover controller/node controller. Master board 202, in turn, uses those instructions to control coil boards 204 and 206. Master board 202 also receives sensor data from coil boards 204 and 206. In this example, there are five coil boards 204 associated with an outside track straightaway section, and one coil board 204 associated with an interior track straightaway section. Coil board 206 controls the switching track section. Each of coil boards 204 has a series of coils arranged in a line, and an array of Hall Effect sensors. The coils are powered by local drive circuitry (e.g., high current amplifiers) on coil boards 204, and are activated, sequentially, at the control of master board 202 to drive the carrier along a linear track section. Drive magnets in the carrier are attracted or repelled to those coils as the carrier moves along the stainless steel track surface placed above these coils. Hall Effect sensors detect the passing magnets, allowing the coil board to have feedback for controlling the coils. Information collected from the sensors can also be communicated to master board 202. For example, identifying information about a carrier may be communicated, as well as position information about the carrier can be communicated. Coil boards 204 can also have an RFID receiver in some embodiments.

Coil board 206 includes a series of coils, in the same manner as coil boards 204. However, because coil board 204 controls a switching section, coils are arranged in a branch. Furthermore, coil board 206 is responsible for actuating (e.g., actuating a servo motor coupled thereto) the switching member that alters the guide rail in the switching section to redirect the carrier. In some embodiments, the configuration of coils in coil board 206 limits the need for the guide rail that is physically switched. As a carrier is moved into a turn, coils along that route push and pull the carrier in an arc magnetically. The guide rail switching member can assist in that movement but, in some embodiments, it rarely makes contact with the carrier due to the magnetic guide forces. In some embodiments, the coil boards are controlled by master board 202 via an SPI bus, which facilitates serial communication between the master board and the coil boards.

Figure 8:
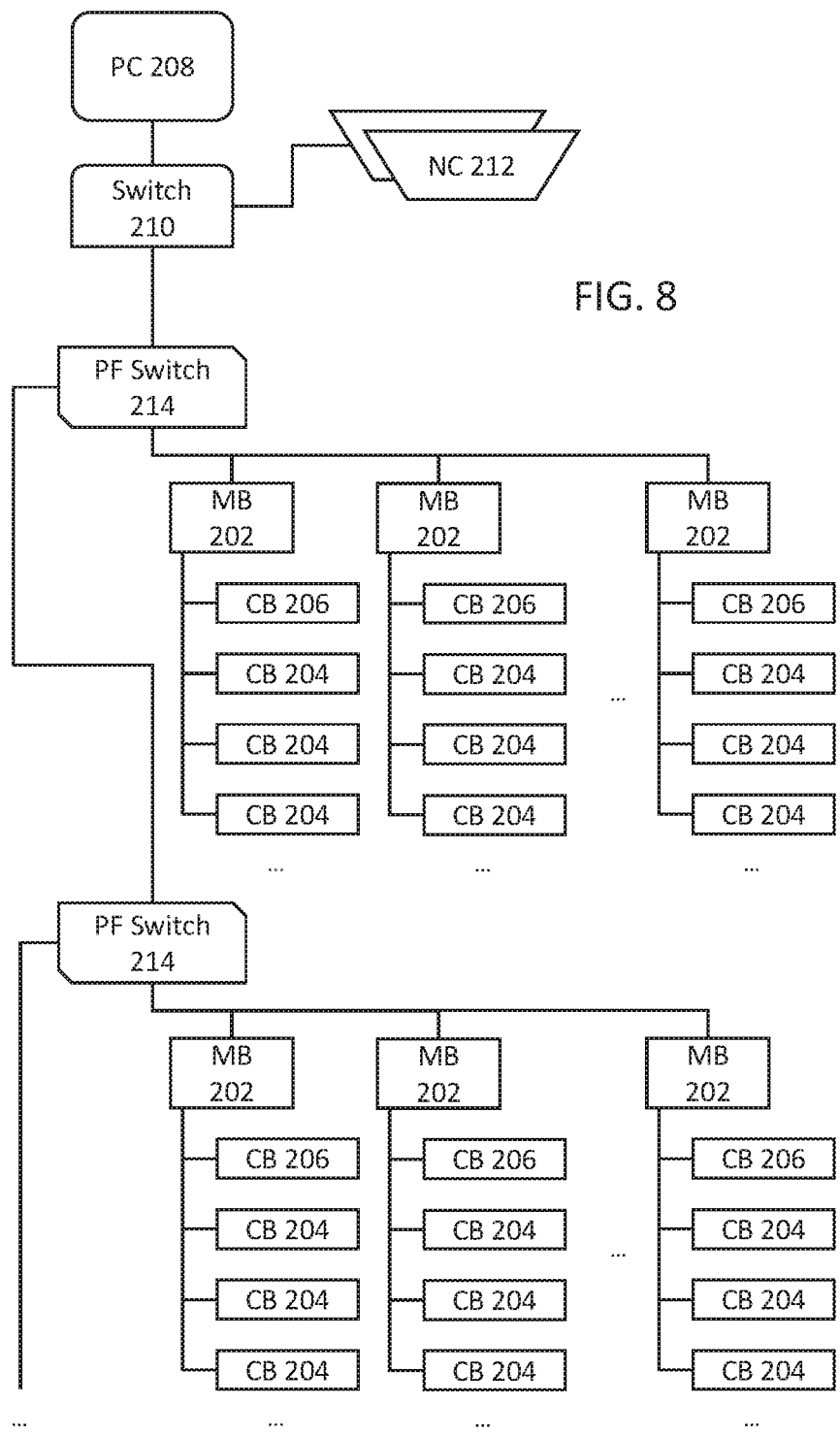
FIG. 8 is an electrical system diagram of an exemplary vessel mover system for use with some embodiments.

FIG. 8 illustrates the network control architecture for the vessel mover system. Vessel mover PC 208 acts as a master controller for the entire vessel mover and provides an interface for an operator or laboratory information system to interact with the vessel mover system. PC 208 can oversee the scheduling of tests and assignment of destinations for individual samples, maintaining a database of status of each sample and tests to be performed. PC 208 provides overall management of the vessel mover, but lower-level management may be left to other modules. PC 208 interacts with other modules within the vessel mover system via Ethernet switch 210. For example, PC 208 can communicate with one or more node controllers 212.

A node controller 212 is responsible for mid-level management and routing of the samples within the vessel mover system. It operates at the overall control of PC 208. However, routing decisions, trajectory decisions, traffic management, etc., are governed by software in node controller 212. Multiple node controllers 212 are illustrated because control can be shared amongst multiple node controllers in a load-balancing fashion. For example, regions of automation track can be assigned to different node controllers, or management of individual carriers can be assigned to different node controllers. In an exemplary embodiment, during normal operation, a single primary node controller 212 is used for all management of the vessel mover system. Meanwhile, a secondary standby node controller 212 is available should the primary node controller go off-line. That secondary node controller can maintain memory that includes the status of all carriers in the vessel mover system to aid in taking over should the primary node controller fail. This provides redundancy and/or hot-swapability, allowing the vessel mover to continue in the event of an off-line node controller.

Node controller 212 communicates with master boards 202 via Ethernet switch 210. As explained above with respect to FIG. 5, local networking within a region of track can be governed by a PFGE switch assigned to each region. In this example, PFGE switches 214 are daisy chained from switch 210 to provide an Ethernet network between node controller 212 and each master board 202. Node controller 212 can communicate over this Ethernet network to give instructions and receive status information about carriers from each master board 202. Each master board 202 then controls local coil boards 204 and 206 via a serial port on that master board. Thus, node controller 212 can control the coils in the track, without communicating directly with each coil board. This aids in scalability of the track system.

As a practical matter, the track of the vessel mover should be at a well-defined height relative to the pipette of an analyzer module. This can be accomplished by providing a track section integral to the analyzer module, or by providing well-defined bracket locations on the analyzer module to allow track section modules to be bolted on in a modular fashion. This allows the pipette to repeatably move relative to an expected position for the bottom of a sample tube (as identified by a model of a sample tube on a typical carrier, or by the information about the tube and carrier determined by a tube characterization station (TCS)). With respect to tube top cups, a reliable vertical position is also important. By placing the bottom of the carrier at a well-known position, and utilizing the characterization information about the tube top cup determined by the TCS, the pipette can reliably interact with the small target of a tube top cup. Moreover, by mounting the bottom and edges of the track at any known position relative to each pipette, a pipette can reliably enter into a tube or tube top cup without interference from sidewalls, and that pipette can reliably determine the fluid height level based on capacitance. A capacitive fluid level sensor utilizes the known conducting properties of a pipette and measures the capacitance when placed in a fluid. By having a reliable tolerance for the bottom of the vessel in which that fluid sets, this capacitive signal can give a reliable estimate of the sample volume remaining.

Figure 9:
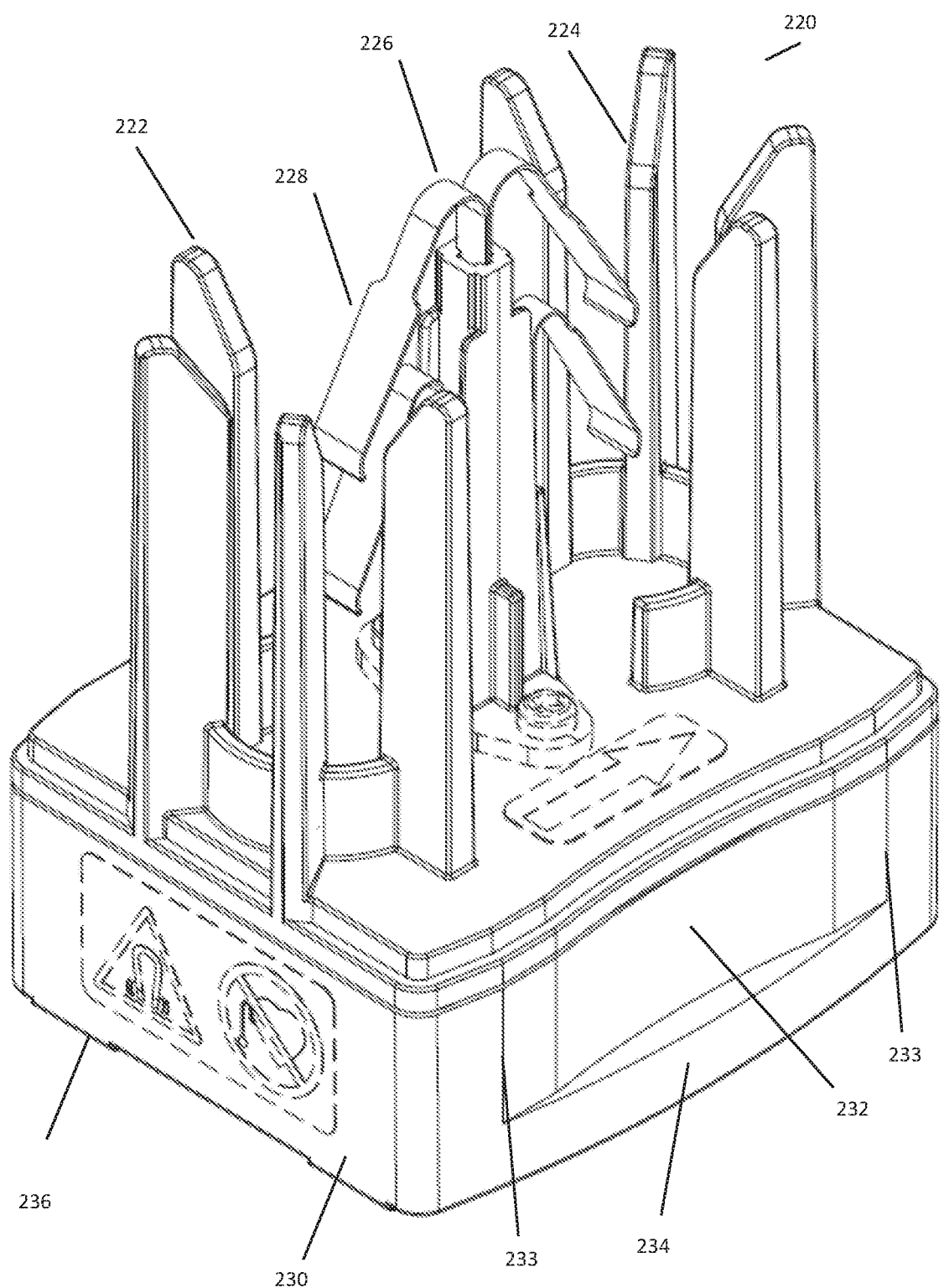
FIG. 9 is a perspective view of an exemplary patient sample tube carrier for use with some embodiments.

The vessel mover system interacts with a plurality of carriers to transport samples, as explained throughout. FIG. 9 shows a perspective view of an exemplary embodiment of a carrier for use with the vessel mover system. Carrier 220 is configured to support place and pick movement of samples into and out of the carrier. The left-hand slot is configured to receive a sample that is placed between a set of four tines 222. The right-hand slot is configured to receive a sample that is placed between the set of four tines 224. These sets of tines are symmetric and mirrors of each other. Between the sets of tines, a central member 226 acts as a fixed tine and includes a set of springs 228 to provide a force to push each sample tube into the set of four tines. While this does not result in centering of different size samples within each sample slot (along the longitudinal axis), the force provided by springs 228 and the shape of tines 224 and 222 will center each sample tube laterally, at the longitudinal axis of the carrier/tines. The arrow shows the longitudinal direction of travel of carrier 220. The tines allow the sample tube to be registered at a fixed location in the longitudinal direction such that the center of the sample tube will depend on the radius of the sample tube, but is easily repeatable based on the size of each sample tube.

Supporting a top plate having these tine sets is body 230. Body 230 acts as a housing that includes any onboard circuitry, such as RFID tags, as well as two or more drive magnets that allow the carrier 220 to form a linear motor in conjunction with coils in the track surface. The sidewalls of body 230 can be adapted to interface track rails. For example, to facilitate alignment during movement in straightaways and around fixed radius curves, the sidewalls of the body can have the following exemplary features. An upper portion of a sidewall of body 230 includes a concave section 232. This concave section can interface the inside corner of the curve, as shown in FIG. 12. Meanwhile, at the vertical edges of concave section 232, short flat sections 233 exist in the sidewall. Moving along a straightaway, a pair of sections 233 on each side of the carrier can help align the carrier along a pair of straight rails. Beneath concave section 232, a convex section 234 provides an interface that can be used to interact with rails on the outside of the curve. It will be appreciated, therefore, that the rails in a curved section can have two heights: the rail on the inside of the curve being placed in a higher location to engage concave section 232, while the rail on the outside of the curve is placed in a lower location to engage convex section 234. In some embodiments, this relationship is switched, providing a concave section lower in the body, while the convex section is located higher in the body to increase lateral stability when going around curves. The exemplary relationship of concave, flat, and convex portions of the sidewalls 232, 233, and 234 may be better understood in the top-down view of FIG. 11.

At the base of body 230, one or more longitudinal sliders 236 can be used to minimize friction between body 230 and the stainless steel track. For example, an ultra-high-molecular-weight (UHMW) polyethylene or Teflon material may be used.

Figure 10:
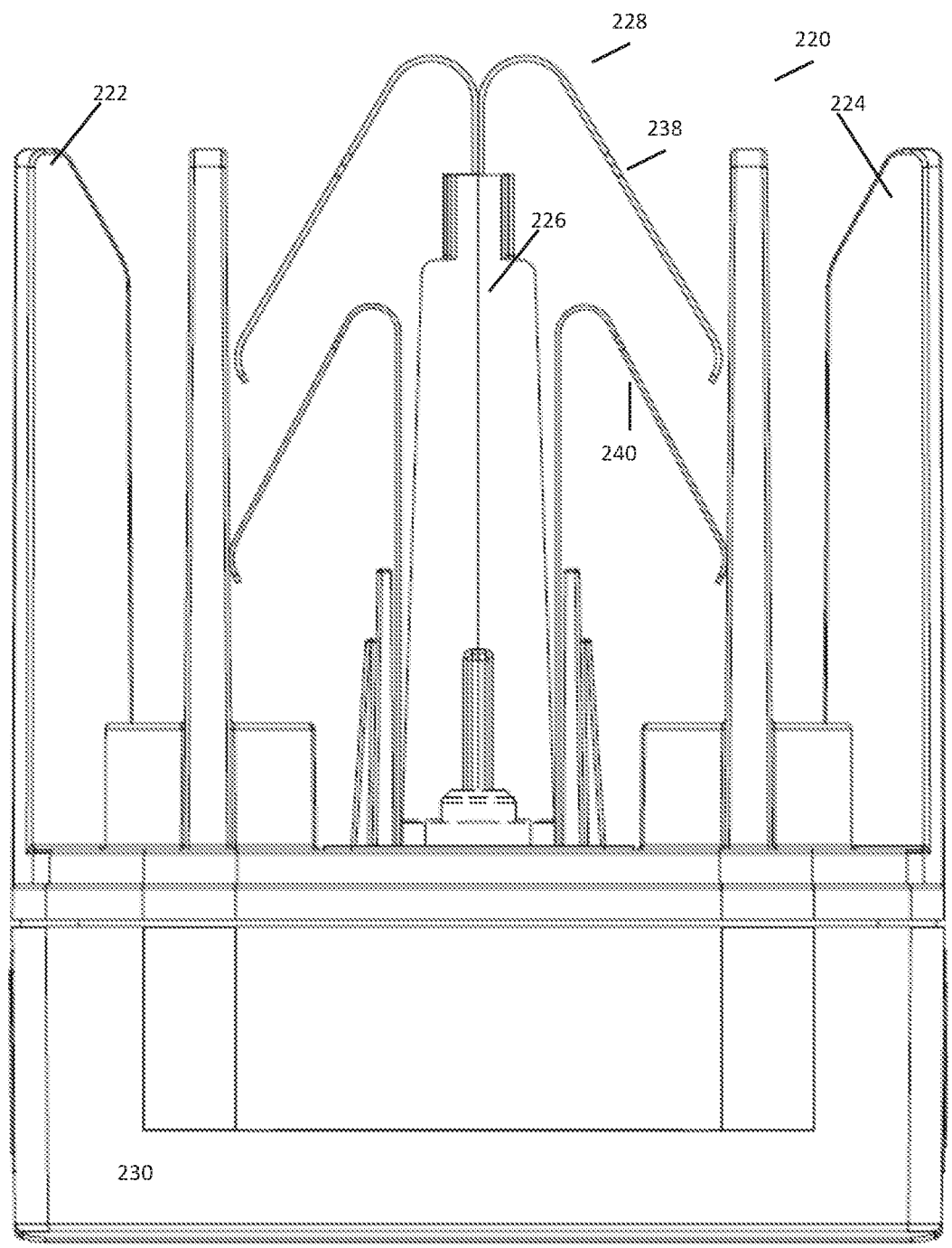
FIG. 10 is a side view of an exemplary patient sample tube carrier for use with some embodiments.

FIG. 10 is a side view of carrier 220. Springs 228 supported by member 226 include two sets of leaf springs, one set for each sample slot. Upper leaf springs 238 provide a longitudinal force to push the top of a tube into tines 222 and 224. Meanwhile, lower springs 240 provide a longitudinal force to push the bottom of the tube into tines 222 and 224. The combination of these two springs ensures vertical alignment of the tube with respect to the vertical alignment of tines 222 and 224.

Figure 11:
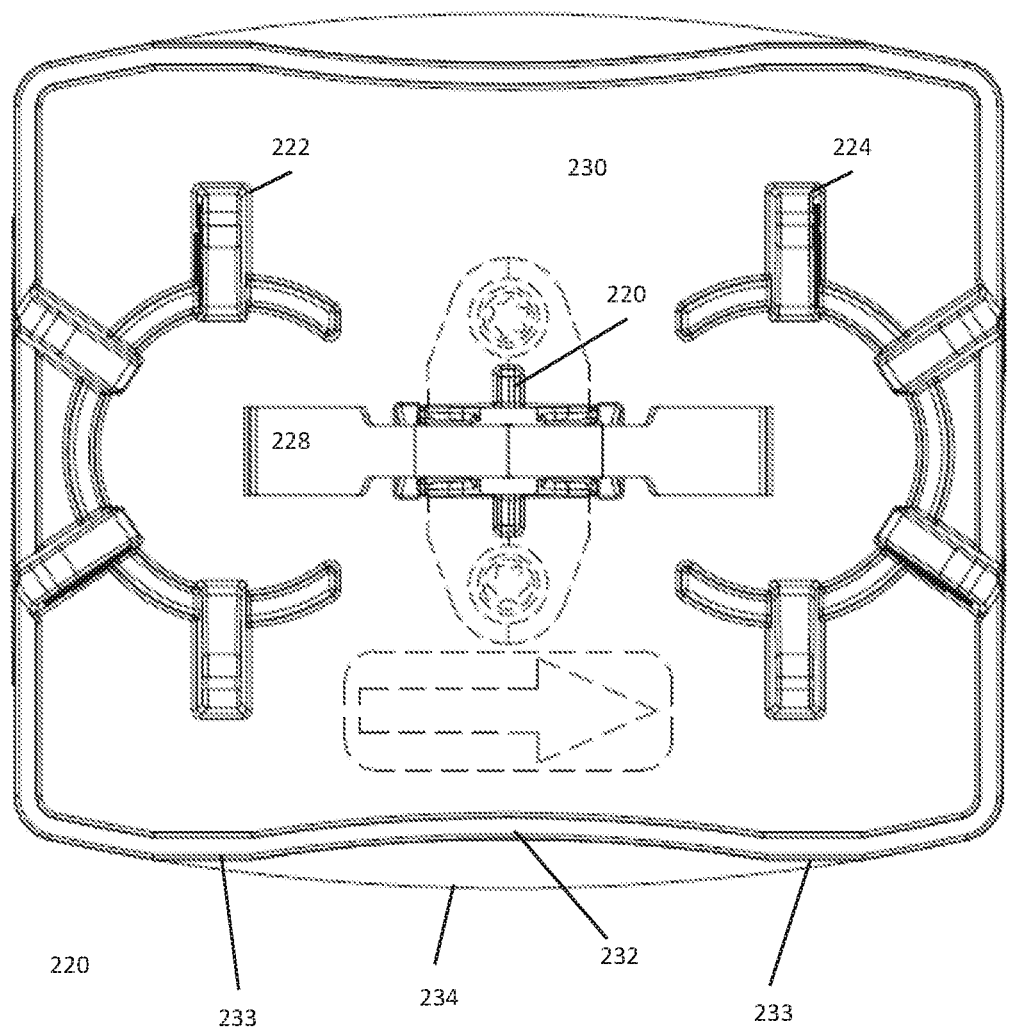
FIG. 11 is a top down view of an exemplary patient sample tube carrier for use with some embodiments.
Figure 12:
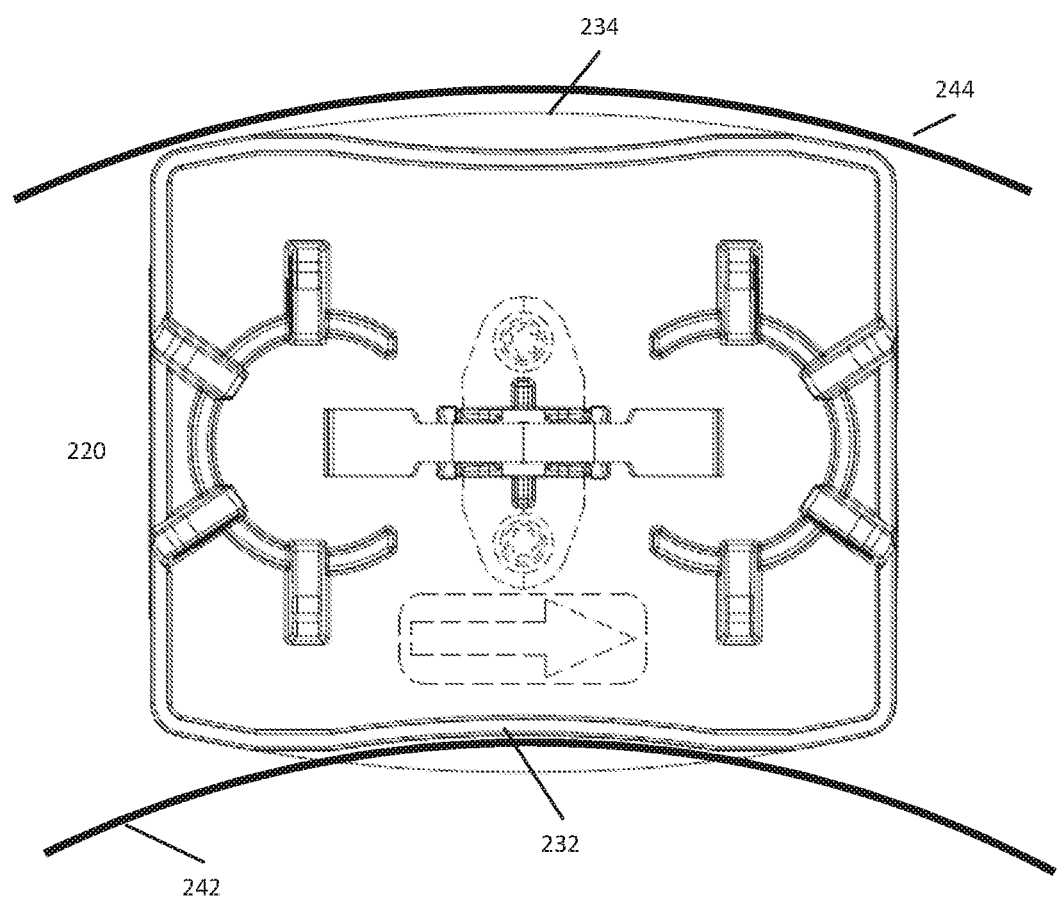
FIG. 12 is a top down view of an exemplary patient sample tube carrier for use with some embodiments.

FIG. 11 is a top down view of exemplary carrier 220 showing the relationship of tines 222, 224 and springs 228. The right-most and left-most pairs (in the orientation of the figure) of tines act to register and center a tube forced by springs 228. Meanwhile, the upper-most and lower-most pairs of tines provide additional security to prevent a tube from tipping over the lateral direction. As can be seen, there are several openings between the tines and springs. This allows various optical views of the tube. When the carrier is placed in the TCS, multiple camera views can be seen through the spaces between the tines to read barcode labels or sense the liquid height in the tube.

In some embodiments, tines 224 and 222 comprise a metal-impregnated or carbon-impregnated plastic. Thus, these tines can be slightly conductive. The conductivity of tines can facilitate location sensing by a pipette and can affect level sensing of fluids using a capacitive level sense. For example, in an exemplary embodiment, the tines, or other structures at the top of the carrier, are made out of approximately 30% (25 to 35%) carbon-filled Lexan resin to enhance capacitive level sensing during sample aspiration. In some embodiments, a range between 20% and 50% carbon filled Lexan resin can be used.

FIG. 12 illustrates rail engagement between the sidewalls of carrier 220 and the side rails of a curved track section. In this example, carrier 220 has an inner side rail 242 and an outer side rail 244. Inner side rail 242 is configured to interface concave section 232 in the sidewall carrier 220. Side rail 242 does not extend all the way to the track surface, allowing the corresponding convex section below concave section 232 to freely pass underneath side rail 242. Meanwhile, outer track section sidewall 242 engages convex section 234 and extends substantially all the way to the track surface. This allows alignment of the carrier 220 in curves by providing physical interfaces to guide rails with radiuses substantially the same as those of the guide rails. This minimizes rattling, oscillations, lateral impacts, etc., when going around a curve.

Figure 13:
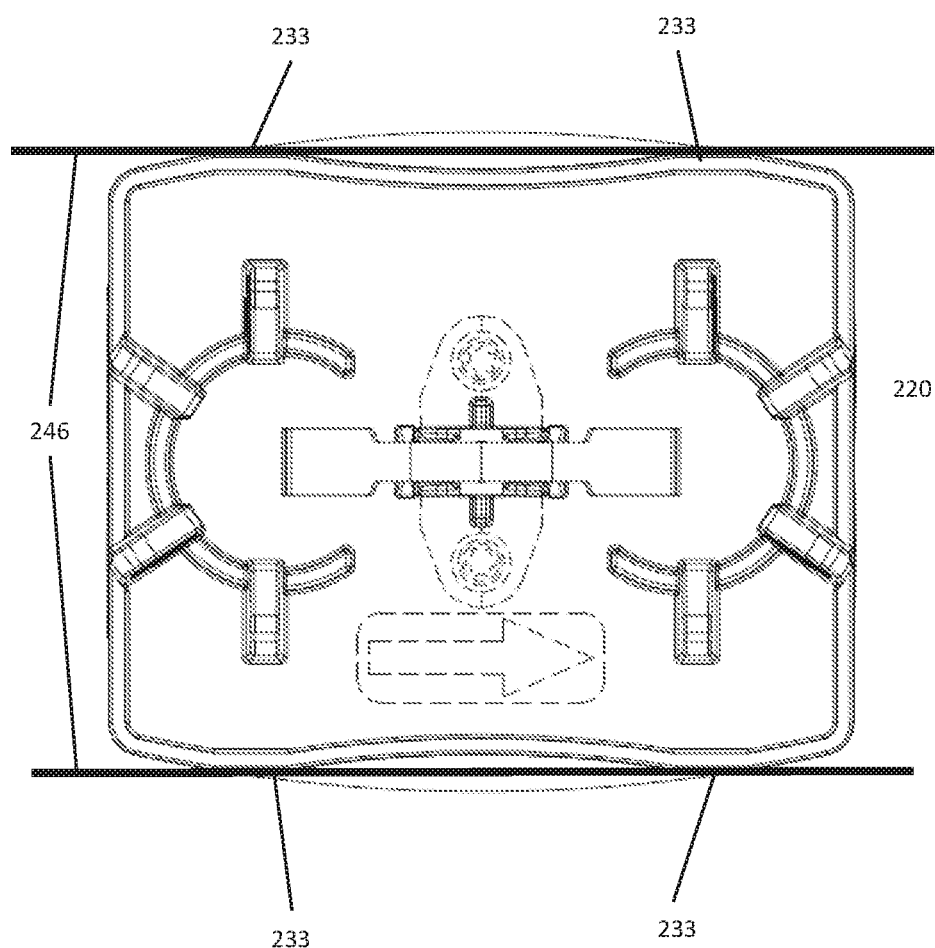
FIG. 13 is a top down view of an exemplary patient sample tube carrier for use with some embodiments.

FIG. 13 illustrates rail engagement between the sidewalls of carrier 220 and the side rails of a straight track section. In this example, flat sidewall sections 233 engage the parallel, flat sidewalls 246 of the track section. This provides four points of interaction between the carrier and sidewalls, assisting in aligning the carrier in the direction of travel.

The VM system and the carriers may be used to assess, and even predict, the health of the vessel mover system or its parts. Via communication from one or more of the various components, such as the coil boards, master boards, node controllers, controller modules, host PCT, vessel mover manager software, linear motors, Ethernet switches, sensors, Hall effect sensors, switching mechanisms, power failover gigabit Ethernet switches, thermometers/thermocouples, humidity sensors, etc., with a local or remote monitoring station (e.g. computer), the current status of the VM system may be assessed in near real-time, and data can be collected, stored, and analyzed for identifying current or future trends in an effort to predict maintenance events before they occur.

In extreme cases, when immediate servicing is required, the monitoring station can be provided with automated systems that react immediately by any or all of shutting down the unit, posting an alarm (e.g., audible or visual), or posting a warning (e.g., audible or visual). In less extreme cases, the monitoring station may simply post information for review by an operator who then can establish priorities based upon other considerations, such as location of maintenance personnel, anticipated time to failure/downtime, etc. In some embodiments, the monitoring station may employ software that evaluates the health of a system and establishes priorities to schedule service and maintenance.

In some embodiments, the remote monitoring station may monitor multiple systems at different locations and potentially different customers simultaneously. In this manner, the IVD manufacturer can implement a service plan for its customers.

The following are exemplary diagnostic use cases. A temperature monitoring device, such as a thermistor, can be installed on each coil board or near each coil. The local master board, or a processor on the coil board, can monitor the values from these temperature devices and report to the node controller of central PC, where all temperature values can be logged at regular intervals, such as every 10 minutes. Software operating on PC 208 can mine this data for temperature values exceeding a thermal threshold that is below the expected failure temperature of a coil, but well above the expected normal operating temperature. Furthermore, by using a log, a rapidly rising temperature can be noted and identified as a failure in progress. In both scenarios, software can alert an operator or automatically place a service call and await for further instructions. Similarly, multiple thresholds can be used whereby a service call can be placed before the board is in a failure state and normal operation can continue, so long as a more severe threshold has not been reached yet. In each case, the failing coil board can be identified by a location and/or unique ID that assists in later service of the board.

Similarly, coil board impedance can be monitored to look for changes in the log indicating potential failure, and service can be requested based on software analysis of the log. Similarly, the magnetic coupling efficiency of each coil can be tested at regular intervals, and the results logged for software analysis. The magnetic field from coils driven with high currents can be measured by Hall Effect sensors in close proximity to the coil. When under test, a coil board applies a current to coils on the board, one at a time, and measures the change in measured magnetic field with an associated Hall Effect sensor. Once all the coils are powered sequentially on a coil board, the node controller reports the measured coupling between coils and Hall Effect sensors.

Each of these tests can be done automatically by the master boards on a regular basis or upon request by an operator or central software.

Figure 14:
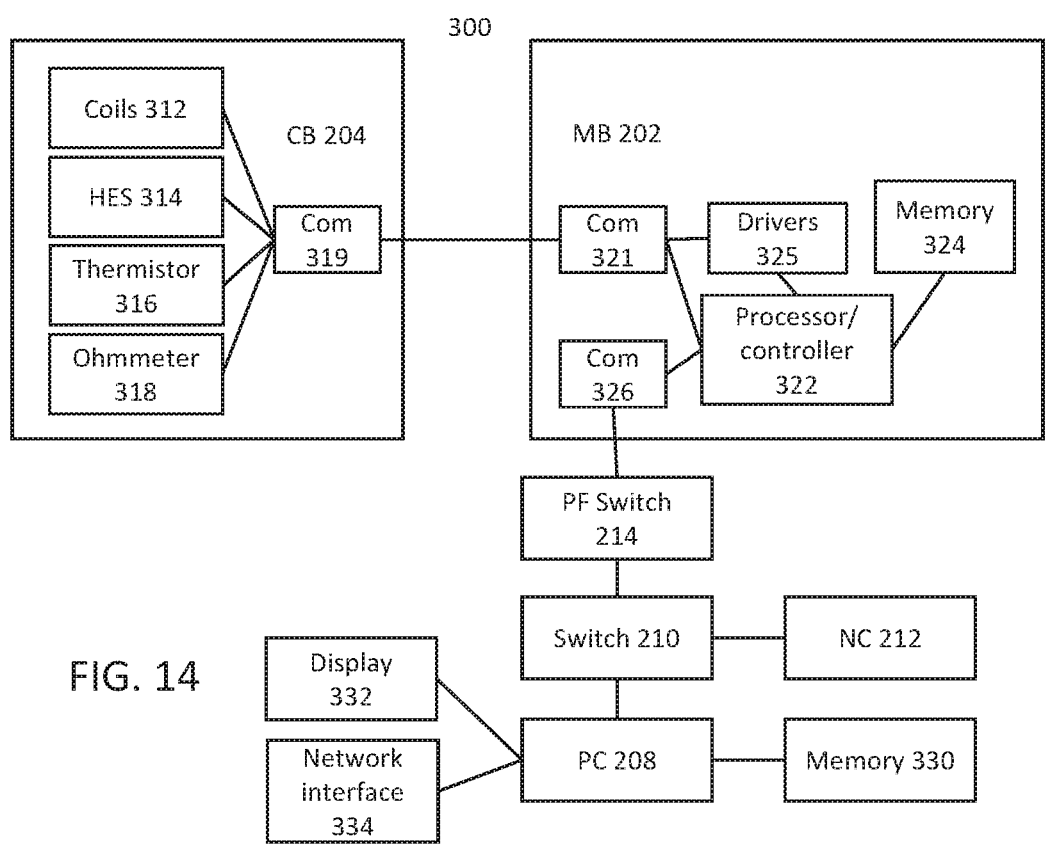
FIG. 14 is a system diagram of an exemplary automation track system for use with some embodiments.

FIG. 14 is a system diagram of an exemplary vessel system that includes details about how the sensors self-diagnosis of the vessel is vessel mover system, and in particular, conditions of the coil board, and the magnetic coupling to carrier magnets traversing the track above each coil board. Because of the high current coils used in each coil board, coils can fail and may be prone to thermal issues and magnetic coupling issues as coils fail.

In system 300, coil board 204 contains a plurality of coils 312. These coils are preferably elongated oval shapes, with a long axis aligned laterally, allowing greater density of coils in the longitudinal direction, allowing more precise movement of carriers. A plurality of Hall Effect sensors 314 is placed amongst and adjacent to coils 312. These Hall Effect sensors provide real-time information about magnetic fields in the areas adjacent coils 312. Coils 312 are sequentially activated, such that the magnetic fields around these coils change as the coils are activated and the carrier traverses these coils. As coils fail, magnetic fields detected by nearby Hall Effect sensors can reveal a change over time in the way that magnetic field behaves when coils are activated. By comparing current Hall Effect data for current activations of coils 312 to past Hall Effect data for past activations of coils 312, slow drifts in the quantity and quality of the magnetic field produced by these coils can reveal that coils 312 are gradually wearing out. Similarly, more abrupt changes between current magnetic fields and passed reserved magnetic fields can indicate a more immediate issue, such as a potential short. The amount of change in magnetic performance can indicate the severity of the problem and identify whether or not the coil board must be immediately replaced or scheduled for inspection for potential replacement at a later time, such as during the next routine service call.

Furthermore, Hall Effect sensor data can be logged and compared to past data for a given carrier in traversing the coils. By comparing this log, Hall Effect sensor data can reveal potential problems with the drive magnets contained within the carrier. For example, an abrupt change in the observed magnetic field when a carrier is directly above a coil, compared to past instances of the same condition, can indicate that some damage has occurred to the magnet in the base of that carrier, or that the magnet has become demagnetized in some manner. Demagnetization of the carrier can gradually occur over time and may result in a slow drift in the observed magnetic characteristics over time (e.g., comparing instances of a carrier being in the same position relative to an active coil are compared over the corresponding period of time). If this drift exceeds a threshold, the carrier can be scheduled for replacement during the next service call. The observed magnetic field can indicate poor magnetic coupling outside of expected parameters. By comparing the results for different coils and different carriers, a processor can determine if a coil board or a carrier are the likely cause of the lagging performance of magnetic coupling.

Similarly, one or more temperature sensors, such as thermistors 316 can be placed in the area around and adjacent to coils 312. Observing the temperature of these coils, potential shorts or poor local performance can be observed. For example, a gradual leakage between coils can result in heating of these coils not consistent with past performance or expected performance of the coils. The amount of heating can indicate the severity of the problem and identify whether or not the coil board must be immediately replaced or scheduled for inspection and potential placement at a later time, such as during the next routine service call.

Other sensors, such as ohmmeter 318 or a voltage sensor can be placed within the drive circuitry for coils 312 on the coil board 204. By observing the electrical characteristics of current and voltage to the drive circuitry, potential shorts or errant electrical behavior can be detected by sensors, and appropriate maintenance or replacement activity can be ordered.

Sensor data from coil board 204 can be transmitted to master board 202 via communication interface 319. Communication interface 319 can also include high-current drive signals for coil 312 and any other signals necessary for operational coil board 204 and receipt of sensor information. Communication interface 319 communicates with communication interface 321 on master board 202. The electrical path by which communication takes place can be any conventional means, such as a serial bus interface, allowing master board 202 to communicate with multiple coil boards 204. Sensor data received via Communications interface 321 can be sent to a processor/controller 322. Controller 322 can store sensor information in memory 324. Controller 322 can also control drivers 325, which may be resident on master board 202 or resident on coil boards 202. In this way, controller 322 is responsible for controlling the activation of coils 312 and for receiving and temporarily storing sensor data from coil boards 204.

Commands can be received by master board 202 via communication interface 326. Sensor data stored in memory 324 can also be communicated to PC 208 via this communication interface. Commands for operating coils 312 can be received from node controller 212 via switch 210 and power failover switch 214. Sensor data received from coil boards 204 that is stored in memory 324 can be sent to PC 208 via this same network path. The processor in PC 208 can then store sensor data in memory 330. Memory 330 can store other data about the system, as well as command and status information for operating the vessel mover system.

Data stored in memory 330 can include a real-time log of sensor data received from the plurality of coil boards 204 and the vessel mover system 301. In some embodiments, this log is maintained for a short period of time, such as a minute or an hour. In some embodiments, past logged information can be condensed into averages to identify expected behaviors of sensor data from coil boards 204 for easy comparison by processor 208. By comparing real-time sensor data received from sensors on coil boards 204 to logged sensor data, averages, or an expected model stored in memory 330, anomalous behavior of coil boards 204, where the boards are behaving outside of expected parameters can be identified from the sensor data.

For example, a long-term trend of reduced magnetic field strength from the coils 312 can be determined by observing a trend in Hall Effect sensors 314 the corresponding to a given coil. If this drift exceeds a threshold, PC 208 can determine an appropriate action. Appropriate actions can be defined by a set of rules that may be defined in software. For example, where a magnetic field has been reduced by more than 3% since the coil board has been installed, the coil board can be flagged for inspection during the next routine maintenance. If that magnetic field strength has been reduced by greater than 10%, the coil board can be flagged for immediate replacement. The exact magnitude of these thresholds can be determined based on operational tolerances of vessel mover system 301 or can be determined based on statistical analysis of a vessel mover system 301 in a real world beta test. By logging sensor data for a plurality of coil boards over a predetermined period of time, such as one month, statistical analysis can reveal mean behavior expected for each coil board for each sensor type. Any coil boards behaving in a statistically significant deviation from this mean can be identified as potentially failing. For example, sensor values that are more than one or two standard deviations from the statistical model can be identified as errant and in need of service. The magnitude of the deviation to be used in determining the appropriate corrective action, such as identifying a given coil board by ID number or location for inspection during the next routine maintenance or identifying a coil board for immediate replacement.

Once the processor in PC 208 has analyzed the sensor data (stored in memory 330 and received via switch 210) to identify any coil boards that are performing outside normal parameters, PC 208 then alerts an operator that certain errant coil boards have been identified. This takes place automatically and can be accomplished via a display 332, which displays information about the error and identifies the coil board, or via a network interface 334, allowing PC 208 to send an alert to a local operator via a local network or the Internet, or alert a maintenance technician employed by the manufacturer of the IVD system over the Internet. For example, display 332 can display information about motor status, coil board temperature, and magnetic field strength from the sensor data for any coil board operating outside normal parameters. The choice to display or to send an alert over the network can be in response to a rule that identifies the method to alert an operator based on the severity of the errant performance of coil board. A series of rules and policies can be stored in memory 330, such that PC 208 has a standing protocol for alerting an operator when a coil board behaves differently than expected parameters in various manners. For example, if a magnetic field is expected to be a certain amount when coil is activated, but that magnetic field is less than a threshold amount, a warning can be displayed on display 332. If that magnetic field is less than a lower threshold amount, an email can be sent via a network interface 334 requesting immediate maintenance of the coil board in question. Similar thresholds can be established for temperature and current parameters for each coil or coil board.

Figure 15:
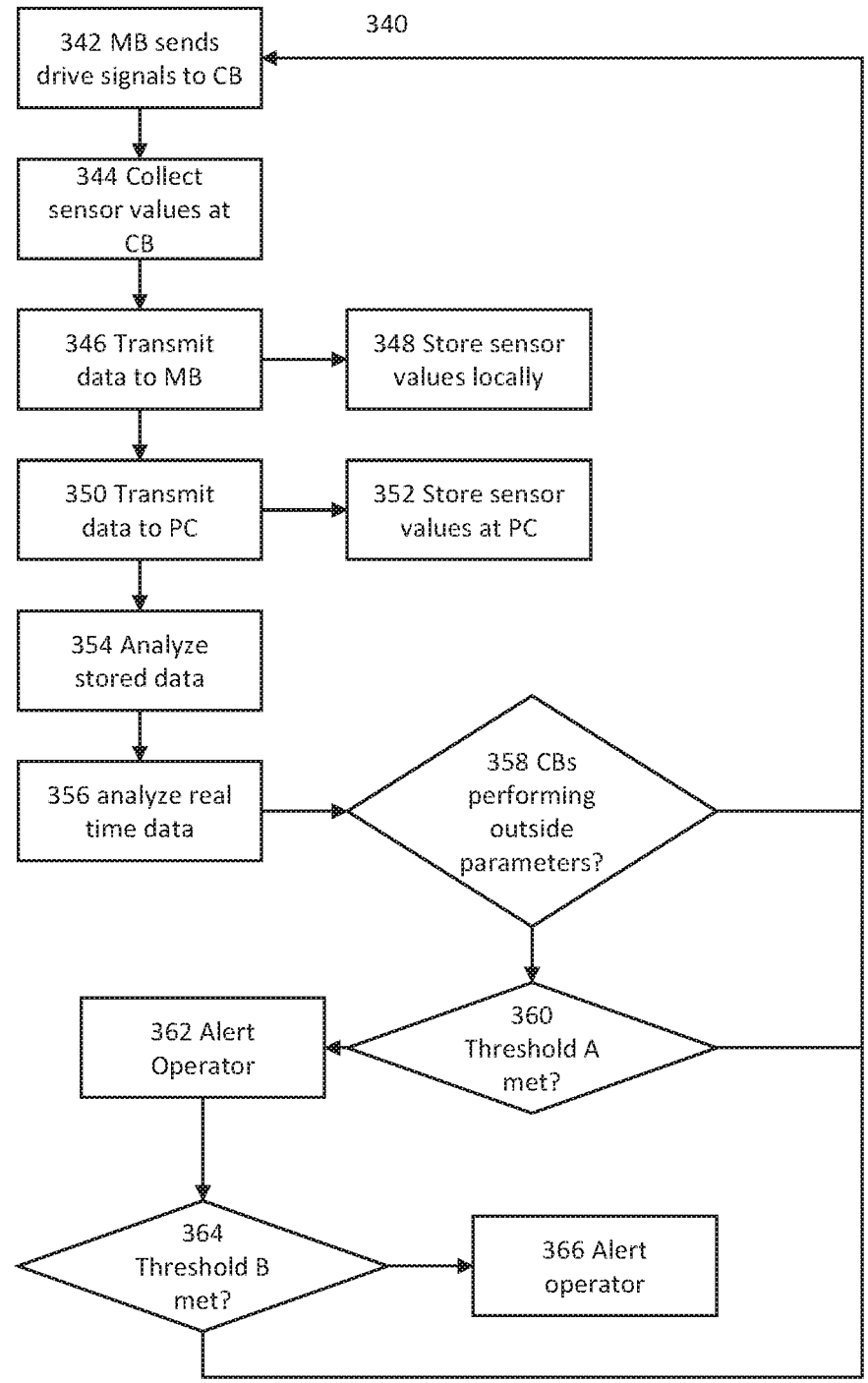
FIG. 15 is a flow chart for operating an exemplary automation track system for use with some embodiments.

FIG. 15 shows an exemplary method 340 for performing maintenance monitoring of an IVD automation system. At step 342, a controller on master board 202 sends drive signals to coil board 204 to sequentially activate coils on that coil board. The selective activation of coils is performed in a synchronized manner to drive carriers on the track above that coil board. At step 344, coil boards 204 collect sensor values that monitor the real-time performance of coils in the coil board. For example, Hall Effect sensors monitor magnetic field performance, thermistors monitor thermal properties, and a voltmeter or ohmmeter monitor electrical properties of the coils or drive signals being sent to those coils. It should be appreciated that Hall Effect sensors sense not only the magnetic field created by a coil, but also the magnetic field created by the driving magnetic of the carrier passing. The combination of these fields can be sensed by the Hall Effect sensor to determine the quality of magnetic coupling between the coil and the magnets. These sensors can identify problems of coil boards or problems with drive signals that may indicate problems with master boards 202 with electrical connection between master boards and coil boards. At step 346, this sensor data is transmitted over a local communications interface to in master board 202. A processor on the master board can store the sensor data in memory or a buffer at step 348, before transmitting the data over the local network to PC 208 at step 350. PC 208 then stores of those sensor values in a database accessible to the processor of PC 208, at step 352. By storing this sensor data in a database or log, PC 208 can then analyze sensor data to look for statistically significant trends in the sensor data, or to provide baseline values when searching for signs of failure within a coil board. This database can include a series of records identifiable by coil board ID and sensor ID to correlate sensor data to each coil board.

At step 354, the processor in PC 208 analyzes the stored data. Exemplary analysis can include calculating a time-varying mean or average for sensor value, standard deviations, or other statistical analysis to help determine if recent/future values are anomalous. At step 356, the processor then analyzes the sensor data as it comes in real time. Exemplary analysis of real-time data includes comparing recent sensor values to past sensor values to determine the existence of the trend, comparing the sensor values to thresholds to determine if sensor values are slipping below a predetermined threshold that has been identified in a rule as a sign of failure, necessitating alerting an operator. Threshold values can be compared to average sensor values, such that instantaneous anomalies in sensor data do not result in erroneous alerts.

At step 358, the processor determines if coil boards are performing outside of expected parameters based on the analysis of the sensor data. The determination of what it means to perform outside parameters can be codified in rules or policies stored in memory. For example, a rule might say that if a coil board has heated beyond a certain temperature value, an operator in the laboratory of the IVD equipment should be promptly notified of the issue. Similarly, a rule may identify the amount of deviation from the mean expected performance of the magnetic field a coil board to trigger remedial actions, such as alerting an operator. All coil boards are performing within expected parameters, the process continues at step 342, allowing additional sensor values to be gathered until an error occurs.

If a coil board is identified as performing outside of expected parameters, rules can dictate the remedial action. In this example, a rule dictates multiple thresholds to classify the errant coil board. At step 360, if a first minor threshold is exceeded, the local operator in the laboratory is alerted at step 362. For example, if a coil board is showing signs of being hotter than normal based on the temperature sensor, but the temperature is not yet high enough to damage the coil board or indicate an immediate problem, a notice can be displayed on a graphical user interface of a console within the laboratory that is used by the operator of the IVD equipment. The operator can then dismiss this notice or it can be added to a log that can then be used during future maintenance. For example, if a coil board later fails, a log of errors associated with the coil board can be maintained and reviewed later by a technician to determine the nature of the eventual failure. At step 364, in some embodiments, the rule can identify an additional threshold that indicates a more severe error. If this threshold is exceeded, a different type of alert can be provided to an operator or to a remote service location at step 366. For example, if the temperature value of the thermal sensor on the coil board indicates that there is imminent risk of thermal degradation to the coil board, a more severe warning or notification sound can be triggered on the local operators display. In some instances, the automation system can be automatically halted as a result of the second threshold is exceeded. Furthermore, the network-based notification can be sent from PC 208 to a remote service location, such as a server maintained by the manufacturer of the IVD equipment. This can alert the manufacturer to immediately send out a technician or call the facility to investigate the error. This prompt notification across a network can be helpful in maintaining customer satisfaction of a user of the IVD equipment, allowing equipment to be promptly repaired to minimize downtime in the event of severe failures. For example, a coil board can be immediately scheduled for replacement or immediate maintenance if the second threshold is exceeded. After all alerts have been provided, the method can return to normal operation, if safe, returning to step 342.

The analysis and notification steps can be carried out by PC 208 for another processor that receives censored data from processor controller 322. This includes embodiments where PC 208 is remote from processor or controller 322. In some embodiments, PC 208 can be separated from master board 202 via any network, including the Internet. In some embodiments, switch to 210 is part of a larger network that allows PC 208 to monitor performance of many master boards, including master boards from multiple automation systems. For example, the processor/PC 208 can be separated from master boards via a large network, such as Internet, or a local network in a laboratory, allowing the processor to handle sensor data from multiple automation systems, including dozens or hundreds of master boards. When coil boards are performing outside of expected radio parameters, this processor can display data pertaining to that master board and coil board or take other reasonable actions, including automatically scheduling a maintenance visit from a technician for a severe error. The display data can be part of a regular console display that is used by an operator in a laboratory to handle any functions pertaining to the IVD system and/or automation system.

Although the invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations that fall within the true spirit and scope of the invention.

We claim:

1. A maintenance monitoring system for an in-vitro diagnostics (IVD) system, comprising:
   an automation system comprising:
   a track along which a plurality of carriers traverse, each carrier having one or more magnets in a base of each carrier, and
   a plurality of coil boards mounted to the track, each board comprising one or more magnetic coils arranged along the longitudinal direction of the track and configured to selectively engage the one or more magnets in the base of each carrier, and at least one sensor;
   at least one controller coupled to each of the plurality of coil boards, the controller configured to selectively activate the magnetic coils of each coil board and to collect sensor data from each sensor of each coil board; and at least one processor configured to store the sensor data in memory,
analyze the sensor data to identify any coil boards that are performing outside normal parameters from the sensor data, and
alert an operator automatically if any such identified coil boards.

2. The maintenance monitoring system of claim 1, wherein the at least one processor alerts the operator by displaying data comprising is any of motor status, coil board temperature, and magnetic field strength.

3. The maintenance monitoring system of claim 1, wherein the at least one processor is separated from the controller by an Ethernet network.

4. The maintenance monitoring system of claim 1, wherein the at least one sensor is a Hall Effect sensor.

5. The maintenance monitoring system of claim 1, wherein the at least one processor is separated from the controller by the Internet.

6. The maintenance monitoring system of claim 1, wherein the at least one processor is further configured to request maintenance across a network if any coil boards are determined to be performing outside normal parameters.

7. The maintenance monitoring system of claim 1, wherein the at least one processor is part of a console with a user interface used by an operator of the IVD system.

8. The maintenance monitoring system of claim 1, further comprising a second independent automation system comprising a second track and a second plurality of coil boards that transmit sensor data to the at least one processor over a network.

9. The maintenance monitoring system of claim 1, further comprising a second independent automation system comprising a second track and a second plurality of coil boards that transmit sensor data to the central processor over a network.

10. A maintenance monitoring system for an in-vitro diagnostics (IVD) system, comprising:
an automation system comprising:
a track along which a plurality of carriers traverse, each carrier having one or more magnets in a base of each carrier, and
a plurality of coil boards mounted to the track, each board comprising a plurality of magnetic coils configured to selectively engage the one or more magnets in the base of each carrier, and at least one sensor;
a plurality of controllers, each coupled to a subset of the plurality of coil boards, the controllers each configured to control the magnetic coils of each coil board in the subset and to collect sensor data from each sensor of each coil board and to transmit the sensor data;
a central processor configured to receive, store, and analyze the sensor data to identify any coil boards that are performing outside normal parameters from the sensor data; and
a user interface configured to alert an operator automatically if any coil boards have been identified.

11. The maintenance monitoring system of claim 10, wherein the central processor alerts the operator by displaying data comprising is any of motor status, coil board temperature, and magnetic field strength.

12. The maintenance monitoring system of claim 10, wherein the central processor is adapted for monitoring two or more IVD systems.

13. The maintenance monitoring system of claim 10, wherein the at least one sensor is a Hall Effect sensor.

14. The maintenance monitoring system of claim 10, wherein the at least one central processor is separated from the plurality of controllers by the Internet.

15. The maintenance monitoring system of claim 10, wherein the central processor is further configured to request maintenance across a network if any coil boards are determined to be performing outside normal parameters.

16. The maintenance monitoring system of claim 10, wherein the central processor is part of a console with a user interface used by an operator of the IVD system.

17. A method for monitoring the health of a vessel mover system in an IVD system comprising:
sequentially driving coils in a plurality of coil boards mounted to an automation track such that the coils propel patient sample carriers;
collecting data from a plurality of sensors on each coil board;
transmitting the data to a monitoring station processor configured to receive, store, and analyze data from the sensors;
analyzing the collected data to identify any coil boards that are performing outside normal parameters; and
alerting an operator automatically if any coil boards have been identified.

18. The method of claim 17, wherein the step of alerting the operator comprises displaying data comprising is any of motor status, coil board temperature, and magnetic field strength.

19. The method of claim 17, wherein the step of alerting the operator comprises requesting maintenance by sending a message to a maintenance facility over the Internet.

20. The maintenance monitoring system of claim 17, wherein the plurality of sensors comprise at least one Hall effect sensor.

* * * * *